US009009874B2

(12) United States Patent
McNeal

(10) Patent No.: US 9,009,874 B2
(45) Date of Patent: Apr. 21, 2015

(54) PROTECTIVE GOGGLES AND LENS ASSEMBLIES WITH ADJUSTABLE VENTILATION HAVING REDUCED VISUAL OBSTRUCTION

(75) Inventor: Joseph R. McNeal, Hailey, ID (US)

(73) Assignee: Smith Optics, Inc., Ketchum, ID (US)

( * ) Notice: Subject to any disclaimer, the term of this patent is extended or adjusted under 35 U.S.C. 154(b) by 475 days.

(21) Appl. No.: 13/186,168

(22) Filed: Jul. 19, 2011

(65) Prior Publication Data

US 2013/0019387 A1    Jan. 24, 2013

(51) Int. Cl.
*A61F 9/02* (2006.01)

(52) U.S. Cl.
CPC ...................... *A61F 9/028* (2013.01)

(58) Field of Classification Search
CPC .......................................... A61F 9/02
USPC ..................................... 2/434–436
See application file for complete search history.

(56) References Cited

U.S. PATENT DOCUMENTS

| 611,396 | A |  | 9/1898 | Sheldon |  |
|---|---|---|---|---|---|
| 1,996,587 | A | * | 4/1935 | Meyrowitz | 2/436 |
| D141,195 | S |  | 5/1945 | Baratelli |  |
| D141,196 | S |  | 5/1945 | Baratelli |  |
| D149,713 | S |  | 5/1948 | Welvang |  |
| 2,613,354 | A |  | 10/1952 | Kidzuz et al. |  |
| 3,517,393 | A | * | 6/1970 | Beauchef | 2/436 |
| D228,584 | S |  | 10/1973 | LeBlanc |  |
| 4,707,863 | A | * | 11/1987 | McNeal | 2/436 |
| D319,449 | S |  | 8/1991 | Millar |  |
| 5,245,709 | A |  | 9/1993 | Shipcott |  |
| 5,363,512 | A |  | 11/1994 | Grabos, Jr. et al. |  |
| D372,928 | S |  | 8/1996 | Brune et al. |  |
| 5,542,130 | A | * | 8/1996 | Grabos et al. | 2/436 |
| D377,036 | S |  | 12/1996 | Leonardi |  |
| 5,689,834 | A |  | 11/1997 | Wilson |  |
| D401,607 | S |  | 11/1998 | Miniutti |  |
| D403,689 | S |  | 1/1999 | Mage |  |
| 5,867,841 | A | * | 2/1999 | Chiang | 2/436 |
| 5,929,963 | A |  | 7/1999 | McNeal |  |
| 5,949,514 | A |  | 9/1999 | Wargon |  |
| D432,156 | S |  | 10/2000 | Conway et al. |  |
| D435,058 | S |  | 12/2000 | Green et al. |  |

(Continued)

FOREIGN PATENT DOCUMENTS

| JP | 2001-231905 | 8/2001 |
|---|---|---|
| JP | 4446262 | 1/2010 |

(Continued)

OTHER PUBLICATIONS

International Search Report and Written Opinion dated Feb. 26, 2013 for Application No. PCT/US2012/047217.

*Primary Examiner* — Katherine Moran

(74) *Attorney, Agent, or Firm* — Dorsey & Whitney LLP

(57) ABSTRACT

Lens assemblies and goggles are disclosed. One example lens assembly includes a lens having a plurality of vent openings and having a button opening elongated in shape. A button configured to fit and slide in the button opening includes a portion that extends through the lens and terminates in a button end. A shutter having a plurality of vent openings and a button attachment opening is attached to the button end at the button attachment opening. The vent openings of the shutter overlap the vent openings of the lens with the button in a first position and the vent openings of the lens covered by the shutter with the button in a second position.

23 Claims, 13 Drawing Sheets

(56) References Cited

U.S. PATENT DOCUMENTS

| | | |
|---|---|---|
| D437,871 S | 2/2001 | Tortorella |
| D439,597 S | 3/2001 | Marcum |
| D454,905 S | 3/2002 | Lueking |
| D458,952 S | 6/2002 | Iwanaga |
| D462,081 S | 8/2002 | Wolfe |
| 6,601,240 B2 | 8/2003 | Tsubooka |
| 6,611,966 B1 | 9/2003 | Yamamoto et al. |
| D512,738 S | 12/2005 | Diebel |
| D522,039 S | 5/2006 | Shinya |
| D527,758 S | 9/2006 | Fuchs |
| D533,572 S | 12/2006 | Howard et al. |
| 7,181,779 B2 * | 2/2007 | Hussey .............................. 2/436 |
| 7,188,947 B1 | 3/2007 | Chen et al. |
| D544,013 S | 6/2007 | Curci |
| D547,342 S | 7/2007 | Love |
| 7,241,007 B2 | 7/2007 | Cody |
| D548,251 S | 8/2007 | Broersma |
| D552,662 S | 10/2007 | Woxing |
| 7,320,144 B2 | 1/2008 | Katz et al. |
| 7,380,933 B1 | 6/2008 | Wang |
| 7,686,447 B2 | 3/2010 | Stanley et al. |
| 7,784,934 B2 | 8/2010 | Cauger |
| 7,891,025 B2 | 2/2011 | Kobayashi et al. |
| 8,020,987 B2 | 9/2011 | Lin |
| 8,061,836 B2 | 11/2011 | Tabacchi |
| D653,686 S | 2/2012 | Tobia |
| D653,695 S | 2/2012 | Tobia |
| 8,371,691 B2 | 2/2013 | Chiou |
| 2006/0059608 A1 | 3/2006 | Difilippo |
| 2006/0119948 A1 | 6/2006 | Matsumoto et al. |
| 2008/0086796 A1 * | 4/2008 | Lindahl .............................. 2/428 |
| 2009/0100577 A1 | 4/2009 | Kobayashi et al. |
| 2013/0019387 A1 | 1/2013 | McNeal |

FOREIGN PATENT DOCUMENTS

| | | |
|---|---|---|
| WO | 97/06759 | 2/1997 |
| WO | WO-2013/012928 | 1/2013 |

* cited by examiner

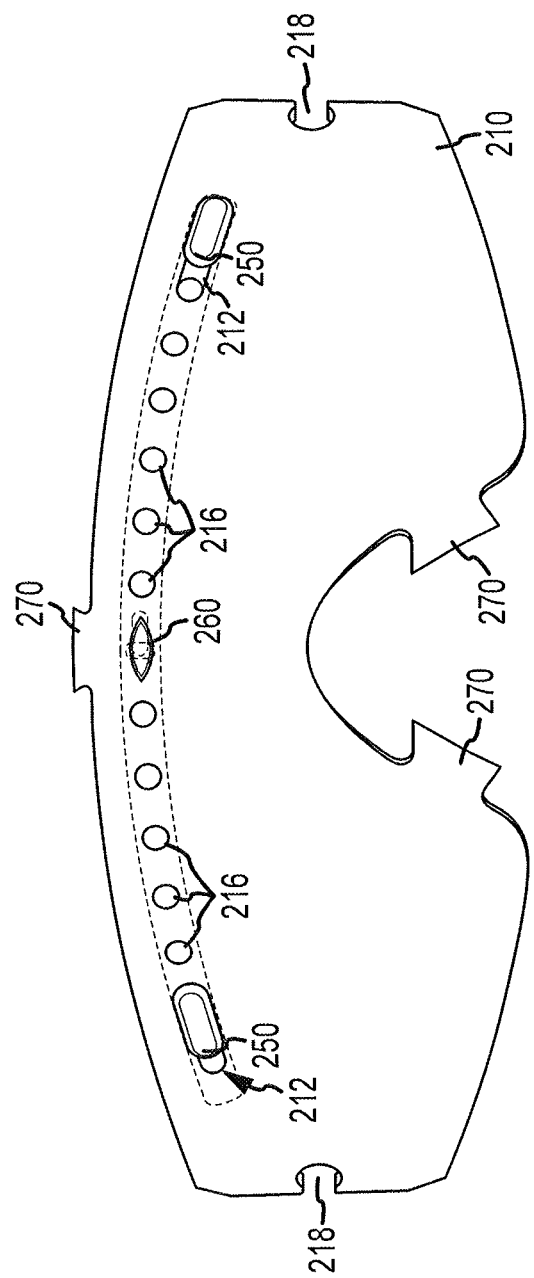

PROTECTIVE GOGGLES AND LENS ASSEMBLIES WITH ADJUSTABLE VENTILATION HAVING REDUCED VISUAL OBSTRUCTION

TECHNICAL FIELD

Embodiments of the invention relate generally to protective goggles, and more particularly, in one or more of the illustrated embodiments, to protective goggles having a lens assembly that includes adjustable ventilation through the lens.

BACKGROUND OF THE INVENTION

Protective goggles are commonly worn during various activities to provide eye protection from debris, projectiles, sharp objects, and other items that can cause eye injury. A drawback to wearing goggles, however, is that condensation may form on an inside surface of the lens when the goggles are worn. The condensation may block the wearer's vision and inhibit the ability to continue the activity until the condensation is cleared. This may require removing the goggles, which may distract from the task at hand and also expose the eyes to potential injury.

Goggles may be vented in some manner to reduce condensation by venting moisture from the goggle interior to the ambient environment. For example, openings may be included in the lens to allow moisture to vent from the goggle interior to the exterior. In some goggle designs, a shutter is used to regulate ventilation through the goggle lens. For example, U.S. Pat. No. 5,542,130 to Grabos, Jr. et al. describes a ventilation adjustment assembly for a goggle that includes a ventilated lens and shutter design. The shutter may be moved between an open position, which allows ventilation, and a closed position, which prevents ventilation.

Although conventional vented goggles may provide adequate ventilation, the design and construction of the ventilation assembly may be more complicated than desirable. Moreover, the assemblies may present a visual obstruction in the wearer's field of vision. Goggles may be made larger to position the ventilation assembly out of the field of vision, however, the resulting goggles may be bulky and awkward in size.

BRIEF DESCRIPTION OF THE DRAWINGS

FIGS. 7A-7C are front views of the goggle lens of FIG. 4.

DETAILED DESCRIPTION

The present application describes goggles and lens assemblies that include a shutter to adjust ventilation through the lens. In some embodiments of the invention, the goggles and lens assemblies may have a simple construction and provide improve field of vision over conventional vented goggles that include vent shutters. Many specific details of certain embodiments of the invention are set forth in the following description and the Figures provide a thorough understanding of such embodiments. One skilled in the art, however, will understand that the present invention may have additional embodiments and that other embodiments of the invention may be practiced without several of the details and components described in the following description.

Figure 1:
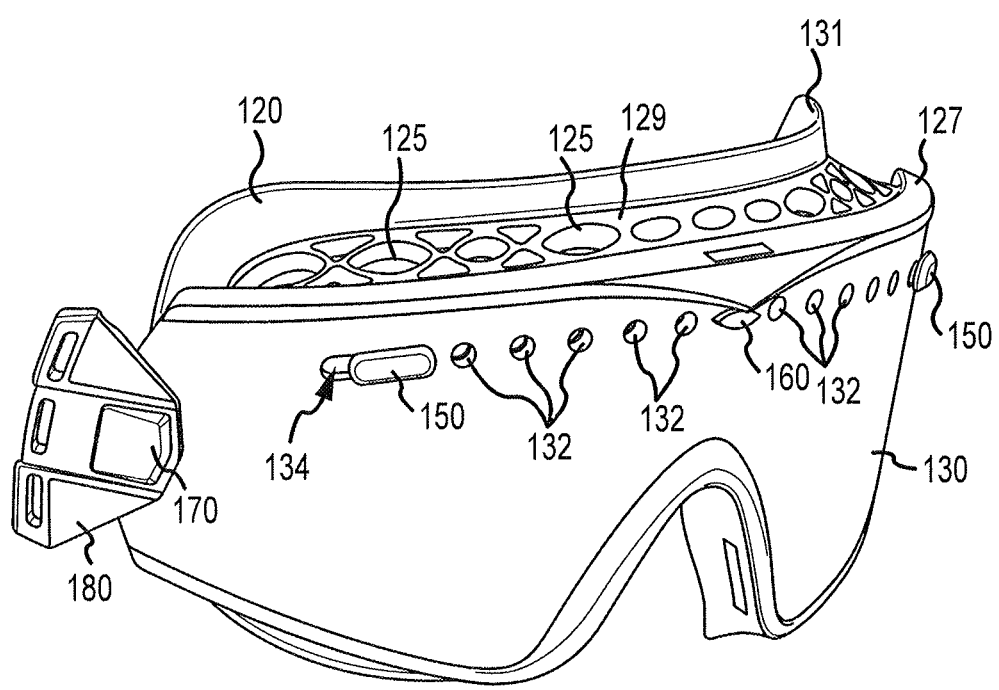
FIG. 1 front perspective view of a goggle according to an embodiment of the invention.
Figure 2:
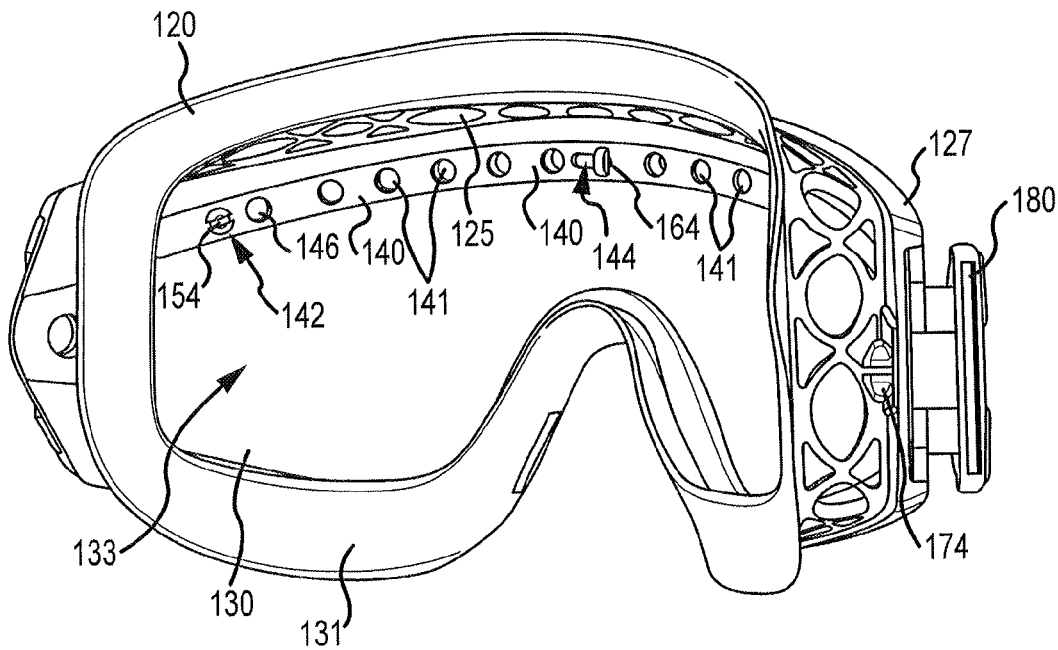
FIG. 2 is a rear perspective view of the goggle of FIG. 1.
Figure 3:
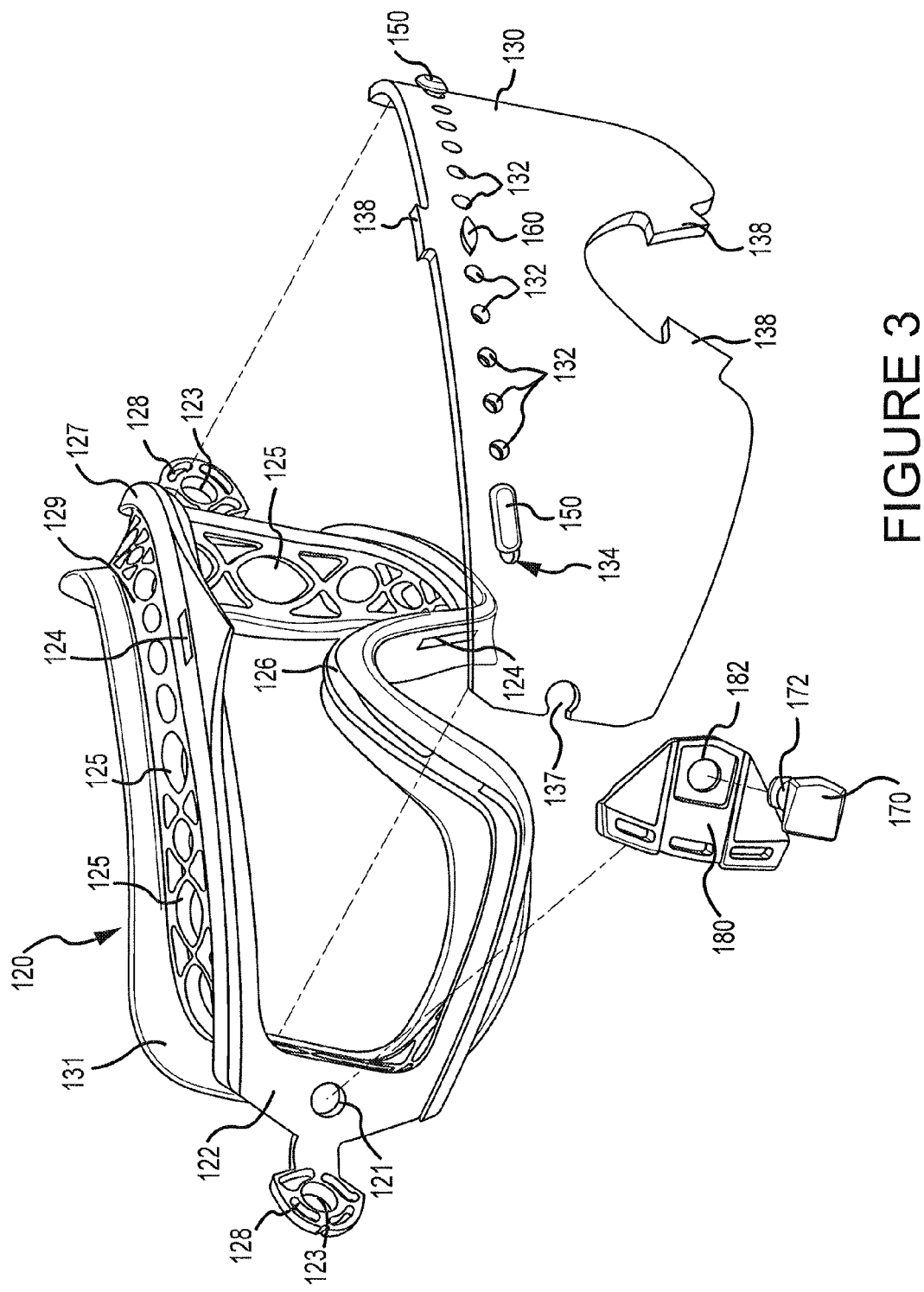
FIG. 3 is an exploded perspective view of the goggle of FIG. 1.

FIGS. 1, 2, and 3 illustrate various views of a goggle 100 according to an embodiment of the invention. The goggle 100 includes a frame 120 formed of a resilient material and a lens 130 that is attached to the frame 120. The frame 120 includes a frame periphery 127 having a lens surface 122 against which the lens 120 is positioned, and may further have slots 124 into which corresponding tabs of the lens 130 fit. A channel 126 is configured to receive an edge of the lens 120. In the embodiment illustrated by FIGS. 1, 2, and 3, the channel 126 is formed proximate a nose recess of the frame 120. The frame 120 may include additional or alternative channels configured to receive an edge of the lens 120.

Vent openings 125 are formed in a stand-off surface 129 that connects the frame periphery 127 to a seal portion 131. The seal portion 131 is configured to be positioned against a face when the goggle 100 is worn. Vent openings 125 allow the environment of an interior region 133 of the goggle 100 to vent to an ambient environment. Attachment tabs 128 and frame openings 121 are disposed proximate to edges of the frame periphery 127. The frame openings 121 and attachment tabs 128 are used to secure the lens 130 to the frame 120. The frame openings 121 may be positioned on the frame periphery 127 to be outside of the interior region 133 of the goggle 100.

The lens 130 includes tabs 138 which fit into corresponding slots 124 to attach the lens 130 to the frame 120. The lens 130 further includes a plurality of openings, for example, vent openings 132, button openings 134, guide opening 136, and pin openings 137. The lens 130 may be a solid lens and the openings 132, 134, 136, and 137 are formed through the entire thickness of the lens 130. The vent openings 132, button openings 134, and guide opening 136 may be positioned generally along an upper periphery of the lens 130 as illustrated in FIG. 1. The openings 132, 134, 136 may be positioned such that they do not substantially impede the line of sight when the goggles 100 are worn. The pin openings 137 are formed at opposite ends of the lens 130 and may extend to a lateral edge of the lens 130, thus forming an opening having a narrow portion proximate the edge of the lens 130 and a wider portion away from the edge.

A shutter 140 is slidably attached to the lens using buttons 150. The shutter includes a plurality of vent openings 141, a guide opening 142, and button attachment openings 144, and button vent openings 146. The vent openings 141 when positioned over the vent openings 132 of the lens allow ventilation through the lens. The button vent openings 146 similarly allow ventilation through the button openings 134 when positioned accordingly. The buttons 150 fit through the button openings 134 and attach to the shutter 140 at button attachment openings 142.

The buttons 150 may be formed having a button shaft 152 and a split anchor end 154 that prevents the button from being pulled free of the shutter 140 after the split anchor end 154 is inserted through the button attachment opening 142. The buttons 150 may be formed from a resilient material so that the split anchor end 154 deflects from a neutral position when inserted through the button attachment opening 142 and returns to the neutral position after being inserted. The split anchor end 154 may be configured to have a first diameter that is approximately equal or less than the button attachment opening 142 when deflected from the neutral position to allow it to be inserted and have a second diameter at the neutral position that is greater than the diameter of the button attachment opening 142 to prevent the button 150 from detaching from the shutter 140 once inserted. The button shaft 152 may have an oblong portion that when the button 150 is received in the button opening 134, the button 150 may be allowed to slide and but prevented from rotating.

A guide post 160 fits through guide opening 136 and through shutter guide opening 144 of the shutter 140. The guide post 160 and the shutter guide opening 144 are configured to guide the sliding movement of the shutter 140. For example, the guide post 160 may include a guide post shaft 162 and an anchor end 164 that fits through the elongated guide opening 136 and guide opening 144 of shutter 140. For example, the guide post 160 may be inserted with the anchor end 164 oriented to fit through the guide openings 136 and 144 (e.g., longitudinal axes of the anchor end 164, and guide openings 136 and 144 generally horizontally oriented). The guide post 160 may then be rotated (e.g., 90 degrees) such that the anchor end 164 is then oriented to prevent the guide post 160 from being pulled back through the guide openings 136 and 144, and to also prevent the shutter 140 from pulling away from the lens 130 during movement (e.g., the longitudinal axis of the anchor end 164 generally vertically oriented).

Pins 170 are used to secure the lens 130 to the frame 120 as well as provide a pivotal attachment for strap connectors 180. One strap connector is illustrated in FIGS. 1, 2, and 3, but the goggle 100 includes another strap connector 180 connected to the opposite edge of the lens 130 and frame 120. The strap connectors 180 are typically attached to an elastic strap (not shown).

Tabs 138 fit in corresponding slots 124 and the edge of the lens 130 is positioned in channel 126. The pin opening 137 and frame opening 121 are also in alignment when the lens 130 is attached. The attachment tab 128 is folded over the lens 130 and an opening 123 of the attachment tab 128 is aligned with the pin opening 137 and frame opening 121. The strap connector 180 is positioned to align an opening 182 of the strap connector 180 with the openings 121, 123, and 137, and pin 170 is inserted. The pin 170 may be configured to have a pin shaft 172 that fits through opening 182 of the strap connector 180, opening 123 of attachment tab 128, pin opening 137, and frame opening 121 when the goggle 100 is assembled.

The pin 170 may be further configured to be locked into place to prevent the pin 170 from being pulled free, which may allow the lens 130 and strap connector 180 to detach. For example, in some embodiments, the pin 170 may include a split anchor end 174 which may deflect from a neutral position to have a smaller diameter sufficient to fit through the openings 123, 137, 182, and 121 when inserted, but return to the neutral position having a larger diameter once inserted to prevent the pin 170 from being pulled out of the openings. In some embodiments, the pin 170 may be further have an oblong portion of the pin shaft 172 configured to have a first dimension (i.e., a narrow dimension) that fits in between the narrow portion of the pin opening 137 and a perpendicular second dimension (i.e., a wide dimension) that does not fit in the narrow portion of the pin opening 137 but fits in the wider portion. In this manner, the pin 170 may be inserted through the openings 123, 137, 182, and 121 in a first orientation, and once inserted, the pin 170 may be rotated (e.g., 90 degrees) to lock the pin 170 in the pin opening 137. An example locking mechanism that may be used is described in U.S. patent application Ser. No. 11/836,729 filed Aug. 9, 2007, which is incorporated herein by reference in its entirety.

Figure 4:
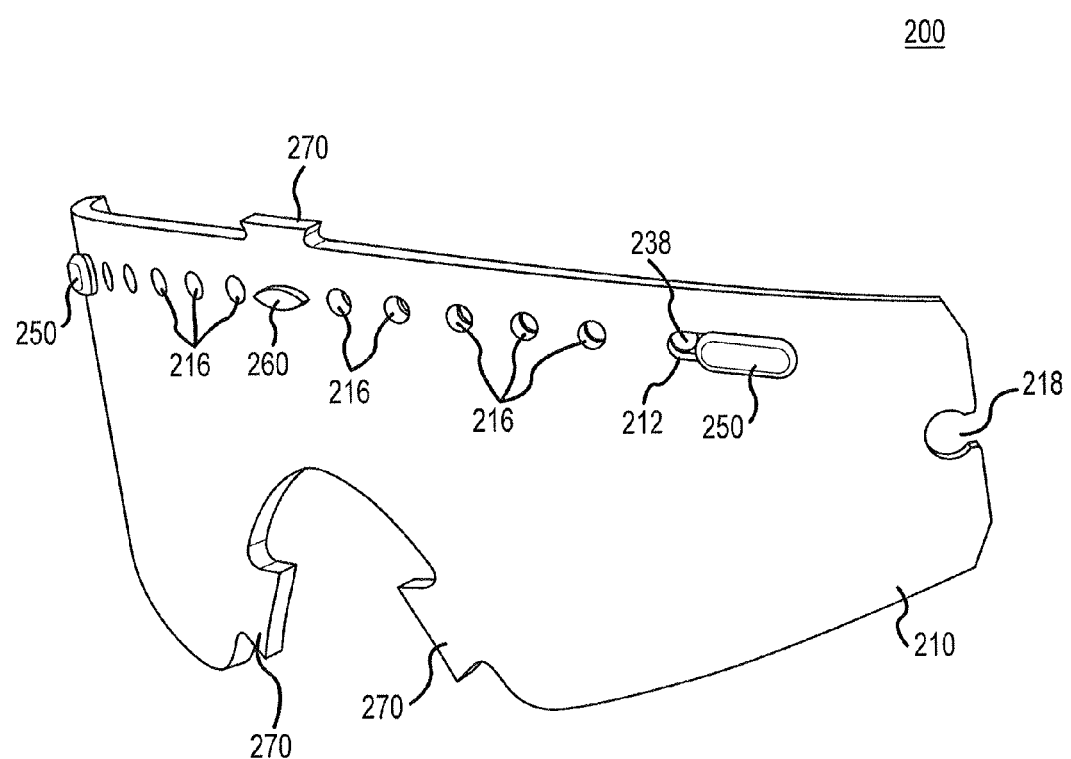
FIG. 4 is a front perspective view of a goggle lens according to an embodiment of the invention.
Figure 5:
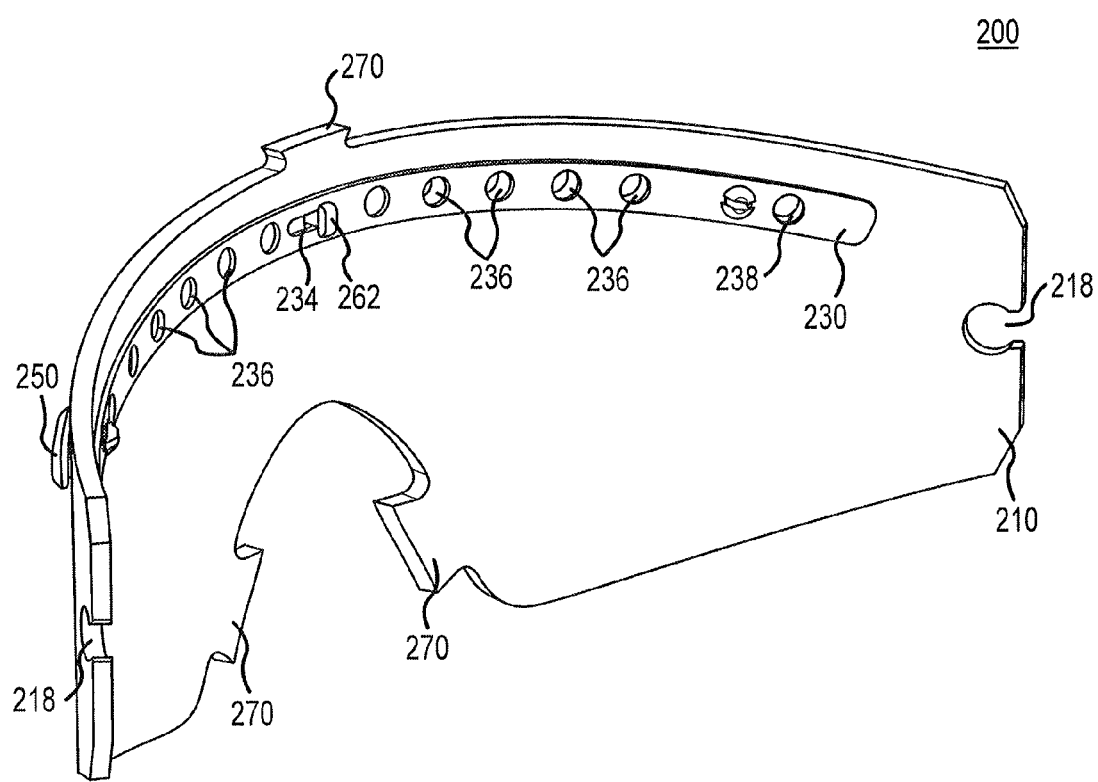
FIG. 5 is a rear perspective view of the goggle lens of FIG. 4.
Figure 6:
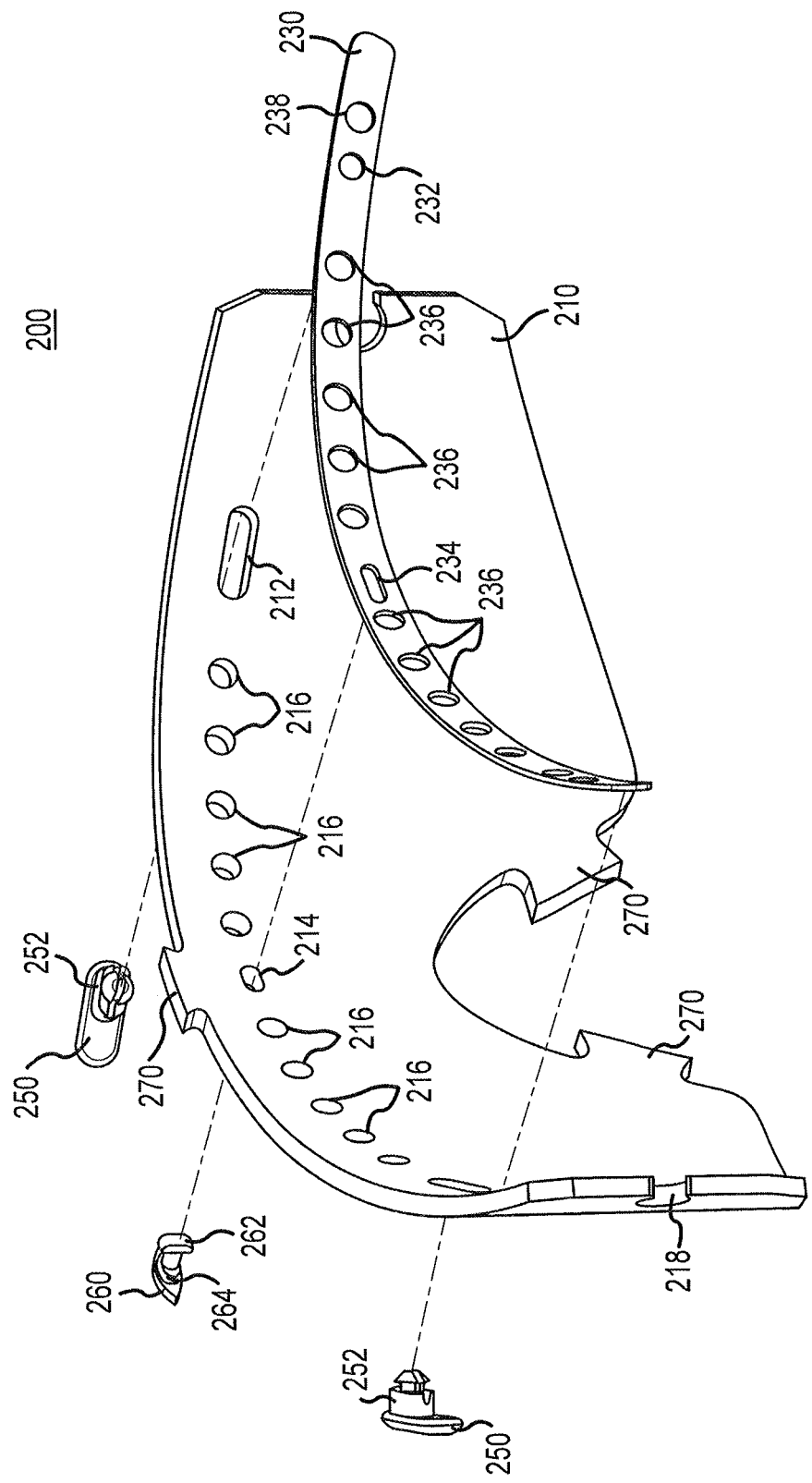
FIG. 6 is an exploded perspective view of the goggle lens of FIG. 4.

FIGS. 4, 5, and 6 illustrate a lens assembly 200 according to an embodiment of the invention. The lens assembly 200 may be used for the lens 30 of the goggle 10 described with reference to FIG. 1. The lens 200 includes a lens 210 and a shutter 230 slidably attached to the lens 210 using buttons 250. A guide post 260 guides the shutter 230 when moved and further prevents the shutter 230 from being pulled away from the lens 210. The lens 210 includes tabs 270 configured to fit into corresponding slots of a frame to which the lens assembly 200 may be attached.

The lens 210 further includes button openings 212, guide opening 214 and vent openings 216. The openings 212, 214, and 216 are positioned proximate an upper periphery of the lens 210, and are generally positioned so that a line of sight through the lens 210 is not obstructed. Pin openings 218 are formed proximate lateral edges of the lens 210 and configured to receive a pin, for example, pin 70 of the embodiment of FIG. 1. The button openings 212 are elongated and configured to receive oblong portions 252 of the buttons 250. The elongated configuration allows the buttons 250 to slide in the button openings 212 but prevent rotation. The guide opening 214 is configured to allow an anchor end 262 of the guide post 260 to be inserted therethrough and to receive an alignment portion 264 to prevent the guide post 260 from rotating once it is rotated into position.

The lens 210 may be formed from a material that provides eye protection and optical transparency. In some embodiments, the lens 210 is formed from an impact resistant material and designed to endure impact from ballistic projectiles without breaking. Conventional materials and designs now known or later developed may be used for the lens 210.

The shutter 230 includes button attachment openings 232 to which the buttons 250 are attached to the shutter 230, and also includes a guide attachment opening 234 through which the guide post 260 is inserted. The shutter 230 further includes vent openings 236 and button vent openings 238. The vent openings 236 may be configured to correspond to the vent openings 216 of the lens 210.

The lens 210 and shutter 230 may have the same opacity and/or shading to reduce the viewing obstruction created by the shutter 230, to the extent that the shutter 230 presents an obstruction due to its positioning on the lens 210. For example, if the lens 210 is clear, the shutter 230 may be clear as well.

As will be described in more detail below, the shutter 230 may be used to adjust ventilation through the openings 212 and 216 of lens 210. The shutter 230 may be moved over a range from a fully closed position to a fully open position. The fully closed position corresponds to where the vent openings 236 and the button vent openings 238 of the shutter 230 do not overlap any portion of the vent openings 216 and button openings 212, respectively, of the lens 210 thereby fully blocking ventilation through any of the openings 212, 216. The vent openings 216 of the lens 210 and the vent openings 236 of the shutter 230 are spaced far enough apart so that the openings 216, 236 do not overlap when the shutter is in the fully closed position. The fully open position corresponds to where the vent openings 236 and the button vent openings 238 of the shutter 230 fully overlap the vent openings 216 and button openings 212, respectively, thereby providing maximum ventilation through the openings 212, 216. Where the openings 236, 238 of the shutter 230 and openings 212, 216 have some overlap ventilation through the lens 230 will be provided.

Figure 7B:
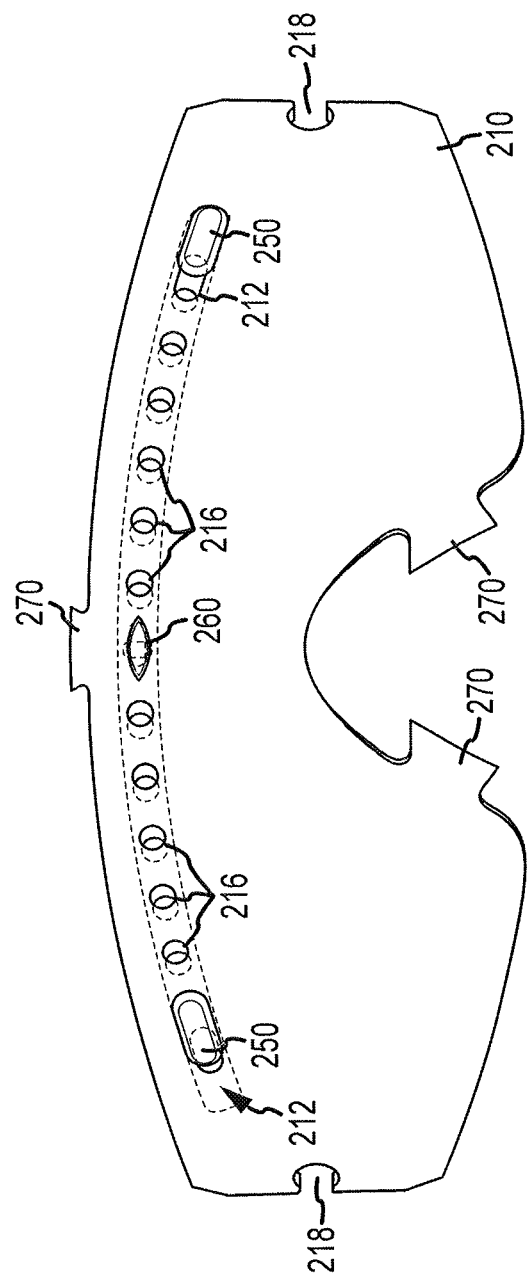

FIG. 7A illustrates the goggle lens assembly 200 with the shutter 230 in the fully closed position. In the fully closed position, the vent openings 236 and button vent openings 238 of the shutter 230 (shown in dashed line) do not overlap any portion of the vent openings 216 or button openings 212 of the lens 210. As a result, when the shutter 230 is moved to the fully closed position the vent openings 216 and button openings 212 are blocked and ventilation through the openings 212, 216 is prevented. FIG. 7B illustrates the shutter 230 in a fully open position. In the fully open position, the vent openings 236 and button vent openings 238 of the shutter 230 overlap the vent openings 216 and button openings 212 of the lens 210. Moving the shutter 230 to the fully open position allows ventilation to occur through the openings 212, 216.

Figure 7C:
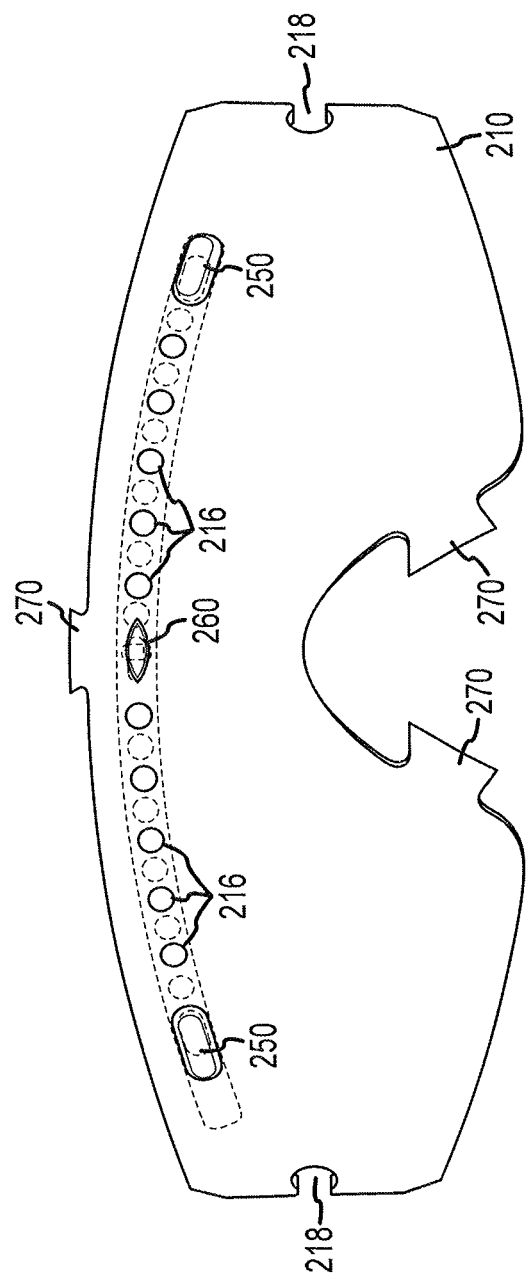

FIG. 7C illustrates the shutter 230 in an intermediate position between the fully closed position of FIG. 7A and fully open position of FIG. 7B. In the intermediate position, the vent openings 236 and button vent openings 238 of the shutter 230 overlap at least a portion of the vent openings 216 or button openings 212 of the lens 210. Using intermediate positions may allow for the ventilation through the openings 236, 238 to be regulated. As illustrated by FIG. 7C, the position of the shutter 230 is not limited to being in either the fully closed or fully open positions, and may be moved to intermediate positions. In some embodiments, the shutter may be moved to any intermediate position over the entire range between the fully closed and fully open positions. The shutter 230 may also have preset positions to which the shutter 230 may be moved and positioned. Such preset positions may be provided by including a detent mechanism in the lens assembly 200.

Figure 8:
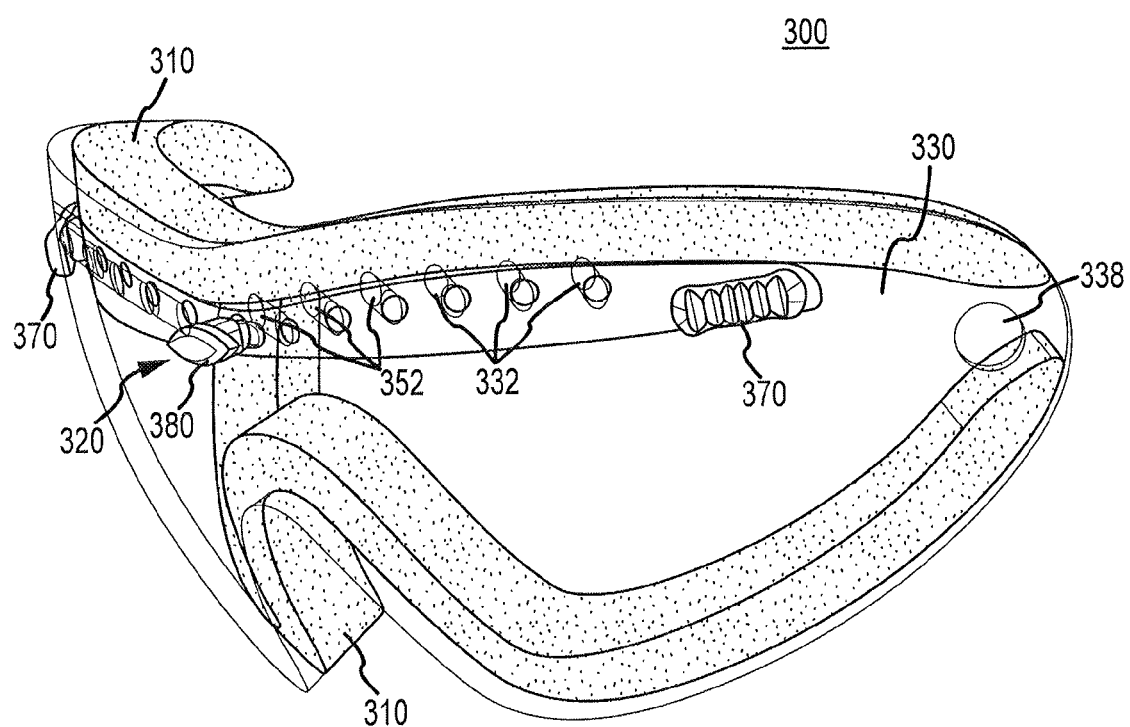
FIG. 8 is a front perspective view of a goggle according to an embodiment of the invention.
Figure 9:
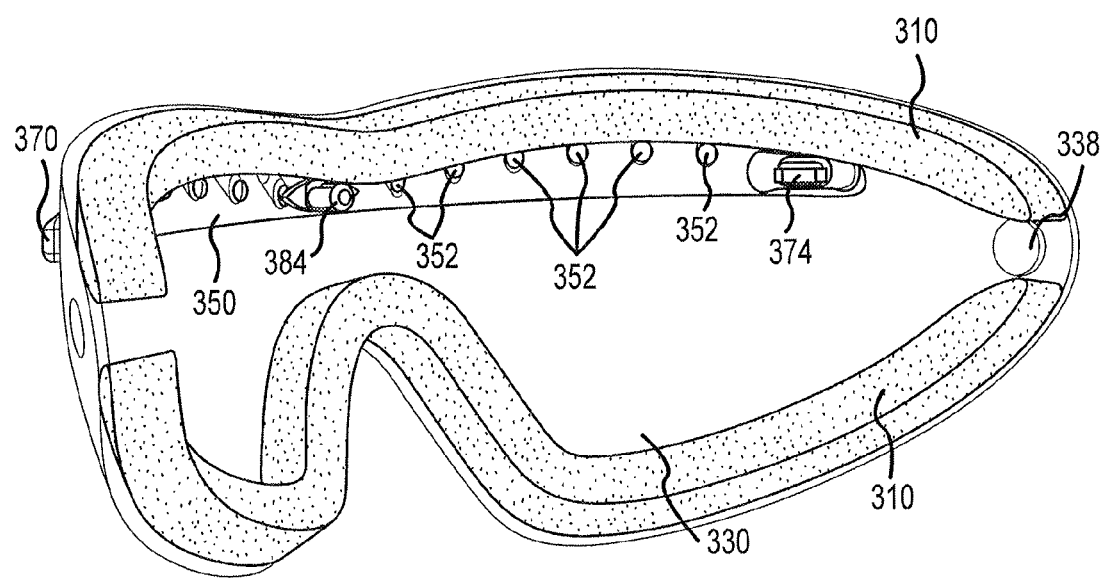
FIG. 9 is a rear perspective view of the goggle of FIG. 8.
Figure 10:
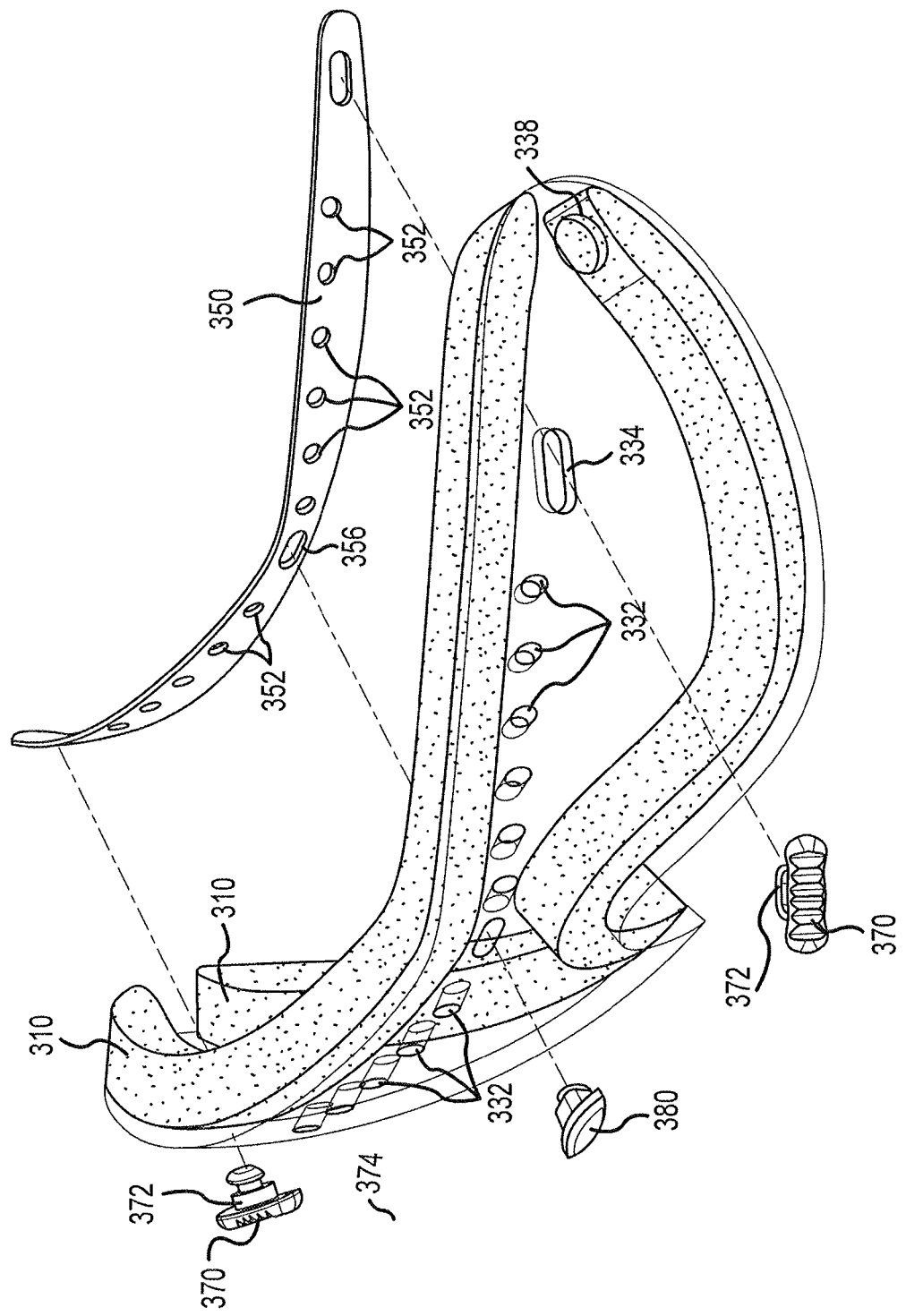
FIG. 10 is an exploded perspective view of the goggle of FIG. 8.

FIGS. 8, 9, and 10 illustrate a goggle 300 according to another embodiment of the invention. The goggle 300 includes a lens assembly 320 and a lens seal 310 attached to a periphery of the lens assembly 320. The lens assembly 320 includes a lens 330 and a shutter 350.

In contrast to the goggle 100, the goggle 300 is "frameless." That is, the lens assembly 320 is not attached to a frame, and the lens seal 310 is used to position the lens 330 when the goggles 300 are worn. The lens seal 310 sets the lens 330 off of a face by a distance approximately equal to the thickness of the lens seal 310. Additionally, the lens seal 310 may be formed from a resilient material and configured to provide comfort and form a seal with the face when the goggles 300 are worn.

Figure 11:
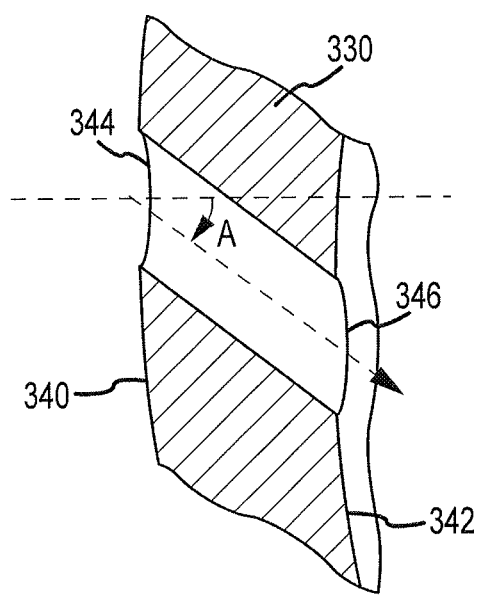
FIG. 11 is a cross-sectional view of a portion of the goggle of FIG. 8.

The lens 330 includes a plurality of vent openings 332, button openings 334, and a guide opening 336. The openings 332, 334, and 336 may be formed proximate an upper periphery of the lens 330 to reduce any obstruction presented by the openings. The vent openings 332 may be angled downward through the thickness of the lens 330. FIG. 11 illustrates a cross-sectional view of a vent opening 332 through the lens 330 according to an embodiment of the invention. The vent opening 332 has an opening 344 on a front lens surface 340 and angles downward at an angle A through the lens 330 to an opening 346 on a rear lens surface 342. In some embodiments, the angle of the vent openings 332 is such that the opening 344 on the front lens surface 340 and the opening 346 on the rear lens surface 342 of the lens do not overlap when viewed from the front of goggles 300. FIG. 11 illustrates such an embodiment. The opening 344 on the front lens surface 340 does not overlap the opening 346 on the rear lens surface 342. In other embodiments, the angle of the vent openings 332 is such that the openings 344, 346 on the front and rear lens surfaces 340, 342 only partially overlap.

The lens 330 further includes strap openings 338 to which a strap (not shown) may be attached. In some embodiments, a strap is connected to the lens 330 through a strap connector that is attached to the goggle 300 at the strap openings 338. In other embodiments, a strap may be connected directly to the lens 330 at the strap openings 338. For example, a strap may include a connection button that fits into the strap openings 338 and may be configured to prevent it from being pulled out of the strap openings 338. Such a connection button may have an end with a split anchor that fits through the strap openings 338.

The shutter 350 includes vent openings 352, button attachment openings 354, and guide attachment opening 356. The shutter 350 may be configured to have an upper edge that generally conforms to an interior outline of the lens seal 310. The shutter 350 may be positioned higher and closer to the lens seal 310 to reduce visual obstruction presented by the shutter. The shutter 350 may be formed from a material having substantially the same opacity and/or shading as the lens 330 to reduce the viewing obstruction created by the shutter 350, to the extent that the shutter 350 presents an obstruction due to its positioning on the lens 330. For example, if the lens 330 is clear, the shutter 350 may be clear as well.

Buttons 370 are positioned in the button openings 334 and attach to the shutter 350 at the button attachment openings 354. The button openings 334 are elongated and allow the buttons 370 to slide thereby moving the shutter 350 laterally. The buttons 370 have an oblong portion 372 that is received in the button opening 334 and is configured to prevent the button 370 from rotating in the opening 334. Each button 370 may include an anchor end 374 configured to fit through the button attachment opening 354 and prevent the button from being detached from the shutter 350 after being inserted.

A guide post 380 is positioned in the guide opening 336 of the lens 330 and the guide attachment opening 356 and guides the movement of the shutter 350. The guide attachment opening 356 is elongated to allow the shutter to slide along the guide post 380. The guide post 380 includes a post portion 382 that is received by the guide opening 336 and guide attachment opening 356 and further includes a guide end 384 that traps the shutter 350 to move generally along the rear surface of the lens 330.

In operation, the shutter 350 may be used to adjust ventilation through the vent openings 332 of the lens by being moved over a range between a fully closed position and a fully open position. In a fully closed position the vent openings 352 of the shutter 350 do not overlap the vent openings 332 of the lens 330, whereas in a fully open position the vent openings 352 fully overlap the vent openings 332. The shutter may also be moved to intermediate positions where the vent openings 332 at least partially overlap the vent openings 332. Ventilation through the vent openings 332 can thereby be controlled by the shutter 350.

From the foregoing it will be appreciated that, although specific embodiments of the invention have been described herein for purposes of illustration, various modifications may be made without deviating from the spirit and scope of the invention. For example, the angled vent openings 332 described with reference to goggle 300 may also be used for vent openings 132 of the goggle 100, as well as for the vent openings 236 of lens assembly 200. Accordingly, the invention is not limited except as by the appended claims.

What is claimed is:

1. A goggle lens, comprising:
a lens having first surface and a second surface opposite of the first surface, the lens further having a plurality of vent openings and having a first button opening elongated in shape and a second button opening;
a first button configured to fit and slide in the first button opening, the first button having a portion extending through the lens from the first surface to the second surface and terminating in a button end;
a second button configured to fit and slide in a second button opening of the lens, the second button having a portion extending through the lens from the first surface to the second surface and terminating in a button end; and
a shutter having a plurality of vent openings, a first button attachment opening, and a second button attachment opening, the shutter proximate the second surface of the lens and the shutter attached to the first button end at the first button attachment opening, the shutter attached to the button end of the second button at the second button attachment opening, the vent openings of the shutter overlapping the vent openings of the lens with the first button in a first position and the vent openings of the lens covered by the shutter with the first button in a second position.

2. The goggle lens of claim 1 wherein the lens further includes a pin opening proximate a lateral edge of the lens, the pin opening have a narrow portion and a wider portion configured to receive a pin having an oblong portion of a pin shaft.

3. The goggle lens of claim 1 wherein the shutter further has a button vent opening, the button vent opening overlapping the button opening of the lens when the button is in the first position.

4. The goggle lens of claim 1 wherein the lens further includes a guide opening and the shutter further includes a shutter guide opening, the guide opening having an elongated shape, the goggle lens further comprising a guide post, the guide post configured to be inserted through the guide opening and the shutter guide opening in a first orientation and rotated to a second orientation to prevent the guide post from being withdrawn.

5. The goggle lens of claim 4 wherein the guide post comprises an elongated anchor end and the guide opening of the lens and the shutter guide opening of the shutter are keyed to the elongated anchor end of the guide post.

6. The goggle lens of claim 4 wherein the guide post comprises a guide post shaft having an elongated portion and the guide opening of the lens is configured to receive the elongated portion.

7. The goggle lens of claim 1 wherein the shutter is attached to the button end at the button attachment opening by the button end inserted through the button attachment opening.

8. The goggle lens of claim 1 wherein each of the plurality of vent openings is formed through the lens from the first surface to the second surface at an angle relative to the first and second surfaces.

9. A goggle, comprising:
a frame including a frame periphery having a lens surface and a lens channel; and
a lens assembly attached to the frame, the lens assembly including a lens abutting the lens surface and having a lens edge received in the lens channel, the lens including vent openings; the lens assembly further including a ventilation shutter configured to cover the vent openings in a first position and expose the vent openings in a second position, the shutter having a substantially same transparency as the lens and being slidably attached to the lens by a pair of buttons, the buttons extending from an exterior lens surface through the lens to an interior lens surface and having button ends extending through the shutter, the button ends having a shape that prevents removal from the shutter.

10. The goggle of claim 9 wherein the lens further includes tabs and the frame further includes corresponding slots into which the tabs of the lens are received.

11. The goggle of claim 9 wherein the frame includes a plurality of openings to vent an interior region to an exterior environment.

12. The goggle of claim 9, further comprising a pin configured to fit through openings in the lens and frame and secure the lens to the frame.

13. The goggle of claim 12, further comprising a strap connector having an opening through which the pin is disposed.

14. The goggle of claim 12 wherein the opening in the lens comprises a narrow region and a wider region, the pin configured to be inserted through the opening in the lens in a first orientation and rotated to a second orientation to lock the pin in the opening of the lens.

15. The goggle of claim 9 wherein the shutter configured to at least partially expose the vent openings of the lens positioned at an intermediate position between the first and second positions.

16. The goggle lens of claim 9 wherein the button ends comprise split anchors having a first dimension suitable to fit through a button attachment opening of the shutter when inserted and a second dimension greater than the first dimension to prevent the button end from being pulled back through the button attachment opening.

17. A goggle, comprising:
a lens having an front surface and a rear surface, and further having a plurality of vent openings extending through the lens between the front and rear surfaces, each of the vent openings are angled downward through the lens from the front surface to the rear surface of the lens;
a shutter proximate the rear surface and configured to cover the plurality of vent openings in a first position and expose the plurality of vent openings in a second position; and
a lens seal attached to the rear surface of the lens along a periphery of the lens and configured to rest on a face of a wearer, wherein, along a lateral periphery of the lens, the lens seal includes a gap between two portions of the lens seal, wherein the gap extends in a direction orthogonal to the rear surface of the lens through an entire height of the lens seal to the rear surface of the lens.

18. The goggle of claim 17 wherein the lens has an upper edge disposed between two lateral edges, the plurality of vent openings positioned proximate the upper edge of the lens.

19. The goggle of claim 17 wherein the shutter is configured to slide laterally over the rear surface of the lens between the first and second positions.

20. The goggle of claim 17 wherein the lens and shutter are clear.

21. The goggle of claim 17 wherein the lens and the shutter have substantially the same degree of transparency.

22. The goggle of claim 17 wherein the vent openings of the lens have circular shaped openings on the front and rear surfaces.

23. The goggle of claim 17, wherein the lens seal includes:
- an upper lens seal attached to the lens along an upper periphery of the lens and ending at a first end point along a lateral periphery of the lens; and
- a lower lens seal attached to the lens along a lower periphery of the lens and ending at a second end point along the lateral periphery of the lens that is spaced apart from the first end point to form the gap.

* * * * *